(12) United States Patent
Sokol Ricci et al.

(10) Patent No.: US 11,180,809 B2
(45) Date of Patent: Nov. 23, 2021

(54) BIOLOGICAL MARKERS FOR IDENTIFYING PATIENTS FOR TREATMENT WITH ABIRATERONE ACETATE

(71) Applicant: JANSSEN PHARMACEUTICA NV, Beerse (BE)

(72) Inventors: Deborah Sokol Ricci, Ringoes, NJ (US); Weimin Li, Norristown, PA (US); Michael Gormley, Mount Laurel, NJ (US); Jayaprakash Karkera, Germantown, MD (US); Michael Schaffer, Fort Washington, MD (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/710,093

(22) Filed: May 12, 2015

(65) Prior Publication Data

US 2015/0322523 A1 Nov. 12, 2015

Related U.S. Application Data

(60) Provisional application No. 61/991,710, filed on May 12, 2014.

(51) Int. Cl.

| | | |
|---|---|---|
| *C12Q 1/6883* | (2018.01) | |
| *A61K 31/58* | (2006.01) | |
| *A61K 31/573* | (2006.01) | |
| *C12Q 1/6886* | (2018.01) | |

(52) U.S. Cl.
CPC .......... *C12Q 1/6883* (2013.01); *A61K 31/573* (2013.01); *A61K 31/58* (2013.01); *C12Q 1/6886* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| | | |
|---|---|---|
| 9,107,918 B2 | 8/2015 | Nishiyama et al. |
| 2009/0215036 A1 | 8/2009 | Stropp et al. |
| 2013/0260376 A1 | 10/2013 | Gupta et al. |
| 2015/0212089 A1 | 7/2015 | Dittamore |
| 2016/0040245 A1 | 2/2016 | Dittamore |

FOREIGN PATENT DOCUMENTS

| | | | |
|---|---|---|---|
| WO | WO 0035473 A2 * | 6/2000 | ........... C12Q 1/6883 |
| WO | 2010-103851 | 5/2010 | |
| WO | WO 2014/151290 A2 | 9/2014 | |
| WO | WO 2015/023710 A1 | 2/2015 | |
| WO | WO 2015/048740 A1 | 4/2015 | |
| WO | WO 2015/112999 A1 | 7/2015 | |

OTHER PUBLICATIONS

May et al (Science (1988) vol. 241, p. 1441).*
Benner et al (Trends in Genetics (2001) vol. 17, pp. 414-418).*
Modrek (Nucleic Acids Reasearch (2001) vol. 29, pp. 2850-2859.*
Cheung et al (Nature Genetics, 2003, vol. 33, pp. 422-425).*
Saito-Hisaminato et al. (DNA research (2002) vol. 9, pp. 35-45).*
Danilla (Journal of Clinical Oncology (2009) vol. 27, abstract 5048).*
Mostaghel (Clinical Cancer Research (2011) vol. 17, pp. 5913-5925).*
Rt2 gene expression assay user manual ((2005) pp. 1-16).*
Adhami (Cell tissues Organs (2011) vol. 194 pp. 232-237).*
GEArray DNA microarrays and as $RT^2$ Real-Time and $RT^2$ End-Point Gene Expression Assay Kits (downloaded Oct. 3, 2016).*
Waltering (Cancer Research (2009) vol. 69, pp. 8141-8149).*
Tombal (annals of Oncology (2012) vol. 23, supplement 10) x251-x258).*
Statistics How to (https://www.statisticshowto.datasciencecentral.com/probability-and-statistics/z-score/; downloaded Jun. 20, 2019).*
Greenbaum et al (Genome Biology 2003, vol. 4, article 117, pp. 1-8).*
Baserga (Journal of Cell Science (1991) vol. 98, pp. 433-436).*
Wang (Nature Cell Biologu (2006) vol. 8, pp. 1359-1368 and supplemental information).*
Li (British Journal of Cancer (2011) vol. 104, pp. 19-23).*
Attard et al., "Phase I clinical trial of a selective inhibitor of CYP17, abiraterone acetate, confirms that castration-resistant prostate cancer commonly remains hormone driven", J Clin Oncol., 2008, 26(28), 4563-4571.
Benjamini et al., "Controlling the false discovery rate: a practical and powerful approach to multiple testing", Journal of the Royal Statistical Society. Series B (Methodological), 1995, 57, 1, 289-300.
Clinical Study Protocol, "A Phase 3 Randomized, Double-Blind, Placebo-controlled Study of Abiraterone Acetate (CB7630) Plus Prednisone in Asymptomatic or Mildly Symptomatic Subjects with Metastatic Castration-Resistant Prostate Cancer", Protocole COU-AA-302, EudraCT No. 2008-008004-41, Jul. 9, 2012, 5 pages.
Cooperberg et al., "Risk assessment among prostate cancer patients receiving primary androgen deprivation therapy", J Clin Oncol, 2009, 27, 4306-4313.
Corey et al., "LuCaP 35: A New Model of Prostate Cancer Progression to Androgen Independence", The Prostate, 2003, 55, 239-246.
Danila et al., "Phase II multicenter study of abiraterone acetate (AA) plus prednisone therapy in docetaxel-treated castration-resistant prostate cancer (CRPC) patients (pts): Impact of prior ketoconazole (keto)", Journal of Clinical Oncology, vol. 27, No. 15S, 2009, 5048, 2 pages.
De Bono et al., "Abiraterone and increased survival in metastatic prostate cancer", N Engl J Med, 2011, 364, 1995-2005.
Ellis et al., "Characterization of a Novel Androgen-sensitive, Prostate-specific Antigen-producing Prostatic Carcinoma Xenograft: LuCaP $23^1$", Clinical Cancer Research, Jun. 1996, vol. 2, 1039-1048.
Feng et al., Targeting fibroblast growth factor receptor signaling inhibits prostate cancer progression, Clin. Cancer Res., 2012, 18(14), 3880-3888.
Green et al., "Androgen action and metabolism in prostate cancer", Mol Cell Endocrinol, 2012, 360, 3-13.

(Continued)

Primary Examiner — Steven Pohnert
(74) Attorney, Agent, or Firm — BakerHostetler

(57) ABSTRACT

Provided herein are methods of predicting a likelihood of survival following treatment with AA and prednisone in a patient having CRPC.

5 Claims, No Drawings
Specification includes a Sequence Listing.

(56) References Cited

OTHER PUBLICATIONS

Li et al., "Development and analysis of androgen receptor (AR) axis biomarkers of circulating tumor cells (CTCs) in Japanese metastatic castration-resistant prostate cancer (mCRPC) patients (pts) treated with abiraterone acetate (AA)", Abstract #129233, https://asco.confex.com/asco/2014/sci/papers/viewpaper.cgi?RecordType=Paper&Recordid, Feb. 4, 2014, 5 pages.

Marin-Aguilera et al., "Identification of docetaxel resistance genes in castration-resistant prostate cancer", Mol Cancer Ther, 2012, 11, 329-339.

Matsubara et al., "A phase 2 trial of abiraterone acetate in Japanese men with metastatic castration-resistant prostate cancer and without prior chemotherapy (JPN-201 study)", Jpn J Clin Oncol, 2014, 44, 1216-1226.

Miyamoto et al., "Androgen receptor signaling in circulating tumor cells as a marker of hormonally responsive prostate cancer", Cancer Discovery, 2012, 2, 995-1003.

Mostaghel et al., "Resistance to CYP17A1 Inhibition with Abiraterone in Castration-Resistant Prostate Cancer: Induction of Steroidogenesis and Androgen Receptor Splice Variants", Clinical Cancer Research, Aug. 2011, 17, 5913-5925.

Pettersson et al., "The TMPRSS2:ERG rearrangement, ERG expression, and prostate cancer outcomes: a cohort study and meta-analysis", Cancer Epidemiol Biomarkers Prev, 2012, 21(9), 1497-1509.

Rathkopf et al., "Updated interim efficacy analysis and long-term safety of abiraterone acetate in metastatic castration-resistant prostate cancer patients without prior chemotherapy (COU-AA-302)", Eur Urol, 2014, 66, 815-825.

Satoh et al., "A phase 2 study of abiraterone acetate in Japanese men with metastatic castration-resistant prostate cancer who had received docetaxel-based chemotherapy", Jpn J Clin Oncol, 2014, 44, 1206-1215.

Schmittgen et al., "Analyzing real-time PCR data by the comparative CT method", Nature Protocols, 2008, 3, 1101-1108.

Tomlins et al., "Recurrent fusion of TMPRSS2 and ETS transcription factor genes in prostate cancer", Science, 2005, 310, 644-648.

Antonarakis et al., "AR-V7 and resistance to enzalutamide and abiraterone in prostate cancer", N Engl J Med, 2014, 371, 1028-1038.

Antonarakis, "Predicting treatment response in castration-resistant prostate cancer: could androgen receptor variant-7 hold the key?", Expert Rev Anticancer Ther, 2015, 15, 143-145.

Attard et al., "Duplication of the fusion of TMPRSS2 to ERG sequences identifies fatal human prostate cancer", Oncogene, Jan. 2009, 27, 253-263.

Bluemn et al., "The androgen/androgen receptor axis in prostate cancer", Curr Opin Oncol, May 2012, 24, 251-257.

De Bono et al., "Abiraterone and Increased Survival in Metastatic Prostate Cancer", New England Journal of Medicine, May 2011, 364(21), 19 pages.

Fizazi et al., "Abiraterone acetate for treatment of metastatic castration-resistant prostate cancer: final overall survival analysis of the COU-AA-301 randomised, double-blind, placebo-controlled phase 3 study", Lancet Oncol, 2012, 13, 983-992.

Gaffney et al., "Identification of Androgen Receptor (AR) Splice Variants, AR Somatic Mutations and TMPRSS2: ETS Fusion Genes in Prostate Cancer", FFPET by qRT-PCR. AACR poster, Apr. 2013, 1 page.

Ryan et al., "Abiraterone acetate plus prednisone versus placebo plus prednisone in chemotherapy-naive men with metastatic cast rati on-resista nt prostate cancer (COU-AA-302): final overall survival analysis of a randomised, double-blind, placebo-controlled phase 3 study", Lancet Oncol, 2015, 16, 152-160.

Ryan et al., "Abiraterone in metastatic prostate cancer without previous chemotherapy", N Engl J Med, 2013, 368, 138-148.

Scher et al., "Evaluation of a Composite Biomarker Panel Including Circulating Tumor Cell (CTC) Enumeration as a Surrogate for Survival in Metastatic Castration-Resistant Prostate Cancer (mCRPC)", 2013, ECCO-ESMO-ESTRO, 22 pages.

U.S. Cancer Statistics Working Group, "United States Cancer Statistics: 1999-2013 Incidence and Mortality Web-based Report", Department of Health and Human Services, Centers for Disease Control and Prevention and National Cancer Institute, 2016, www.cdc.gov, 2 pages.

Scher et al., "Circulating Tumor Cell Biomaker Panel as an Individual-Level Surrogate for Survival in Metastatic Castration-Resistant Prostate Cancer", Journal of Clinical Oncology, Apr. 20, 2015, vol. 33, No. 12, 1348-1355.

Sprenger et al.: 11 The Link Between Androgen Receptor Splice Variants and Castration-Resistant Prostate Cancer ,Hormones and Cancer, vol. 5. 2014, pp. 207-217.

Ripert et al: "Mechanisms of resistance to CYP17AI inhibitors in castrate resistant prostate cancer", castrate resistant prostate cancer; vol. 23, No. Supplement 1, Jan. 1, 2013, pp. S16-S22.

Hornberg et al; Expression of Androgen Receptor Splice Variants in Prostate Cancer Bone Metastases is Associated with Castration-Resistance and Short Survival, PLOS One, vol. 6, No. 4, Apr. 28, 2011; e19059, XP055205987, DOI: 10.1371/journal.pone.0019059 the whole document; 9 pages.

Heinrich et al.: "323 Analysis of Up-Regulated CYP17AI Expression Under Anti-Androgen Strategies in Castration Resistant Prostate Cancer", Journal of Urology; vol. 189, No. 4, May 5, 2013; p. e131.

Sartor, O., et al., Effect of Prednisone on Prostate-Specific Antigen in Patients with Hormone-Refractory Prostate Cancer, 52 Urology 252-56 (1998).

O'Donnell, A., et al., Hormonal Impact of the 17a-hydroxylase/C17,20-lyase Inhibitor Abiraterone Acetate (CB7630) in Patients with Prostate Cancer, 90 Brit. J. of Cancer 2317-25 (2004).

Gerber, G.S. & Chodak, G.W., Prostate Specific Antigen for Assessing Response to Ketoconazole and Prednisone in Patients with Hormone Refractory Metastatic Prostate Cancer, 144 J. Urology 1177-79 (1990).

Efstathiou, E. et al., 'Effects of Abiraterone Acetate on Androgen Signalling in Castrate-Resistant Prostate Cancer in Bone', Journal of Clinical Oncology Feb. 2012, vol. 6, pp. 637-643.

* cited by examiner

BIOLOGICAL MARKERS FOR IDENTIFYING PATIENTS FOR TREATMENT WITH ABIRATERONE ACETATE

SEQUENCE LISTING

The instant application contains a Sequence Listing which has been submitted electronically in ASCII format and is hereby incorporated by reference in its entirety. Said ASCII copy, created on Jun. 2, 2015, is named PRD3334USNP_SL.txt and is 7,840 bytes in size.

TECHNICAL FIELD

Provided herein are methods of predicting a likelihood of longer survival following treatment with abiraterone acetate (AA) and prednisone in a patient having castration-resistant prostate cancer (CRPC).

BACKGROUND

Prostate cancer is the second most common cancer among men in the United States. It is also one of the leading causes of cancer death among men of all races and Hispanic origin populations. In 2010, 196,038 men in the United States were diagnosed with prostate cancer while 28,560 men in the United States died from prostate cancer. (U.S. Cancer Statistics Working Group. United States Cancer Statistics: 1999-2010 Incidence and Mortality Web-based Report. Atlanta (Ga.): Department of Health and Human Services, Centers for Disease Control and Prevention, and National Cancer Institute; 2013.)

A number of therapeutic agents have been approved by the FDA for use in patients with metastatic castration-resistant prostate cancer (CRPC). Among these treatment options are docetaxel with prednisone, abiraterone acetate, cabazitaxel, enzalutamide, mitoxantrone, radium-223, sipuleucel-T, corticosteroids, and ketoconazole. As a result, clinicians and patients are challenged with a multitude of treatment options and potential sequencing of these agents that make clinical decision-making more complex. Methods for identification of therapies associated with improved survival and/or quality of life in particular patient subpopulations would facilitate such challenging decisions.

SUMMARY

Provided herein are methods of predicting a likelihood of survival following treatment with AA and prednisone in a patient having CRPC.

The general description and the following detailed description are exemplary and explanatory only and are not restrictive of the disclosed methods as defined in the appended claims. Other aspects will be apparent to those skilled in the art in view of the detailed description as provided herein.

DETAILED DESCRIPTION OF ILLUSTRATIVE EMBODIMENTS

The disclosed methods may be understood more readily by reference to the following detailed description taken in connection with the accompanying examples, which form a part of this disclosure. It is to be understood that the disclosed methods are not limited to the specific methods, conditions or parameters described and/or shown herein, and that the terminology used herein is for the purpose of describing particular embodiments by way of example only and is not intended to be limiting of the claimed methods. Also, as used in the specification including the appended claims, the singular forms "a," "an," and "the" include the plural, and reference to a particular numerical value includes at least that particular value, unless the context clearly dictates otherwise. The term "plurality", as used herein, means more than one.

It is to be appreciated that certain features of the disclosed methods which are, for clarity, described herein in the context of separate embodiments may also be provided in combination in a single embodiment. Conversely, various features of the disclosed methods that are, for brevity, described in the context of a single embodiment may also be provided separately or in any subcombination.

Provided herein are methods of predicting a likelihood of survival following treatment with AA in a patient having CRPC, the method comprising:
  (a) contacting cDNA from a tumor sample of the patient obtained prior to treatment with AA with a gene chip, wherein said gene chip comprises probes for at least one mRNA biomarker, and wherein the at least one mRNA biomarker comprises ANLN, HSD17B10, NUSAP1, SF1, SRD5A1, UBE2C, CYP17A1 and cofactors group, androgen controlled group, multivariate panel group, or any combination thereof;
  (b) measuring an expression level of the at least one mRNA biomarker;
  (c) comparing the expression level of the at least one mRNA biomarker to an expression level of a reference gene, wherein an increase in the expression level of the ANLN, HSD17B10, NUSAP1, SF1, SRD5A1, UBE2C, CYP17A1 and cofactors group, androgen controlled group, or any combination thereof in the patient sample relative to the expression level of the reference gene indicates an increased likelihood of progression free survival, overall survival, or both for said patient following treatment with AA, or wherein a decrease in the expression level of the multivariate panel group in the patient sample relative to the expression level of the reference gene indicates an increased likelihood of progression free survival for said patient following treatment with AA; and
  (d) treating said patient with a therapeutically effective amount of AA and prednisone.

Also disclosed herein are methods of predicting a likelihood of survival following treatment with AA in a patient having CRPC, the method comprising:
  (a) isolating RNA from a tumor sample of said patient;
  (b) synthesizing cDNA from the RNA;
  (c) measuring an expression level of at least one mRNA biomarker from the tumor sample, wherein the at least one mRNA biomarker comprises ANLN, HSD17B10, NUSAP1, SF1, SRD5A1, UBE2C, CYP17A1 and cofactors group, androgen controlled group, multivariate panel group, or any combination thereof, and wherein the expression level is measured by quantitative RT-PCR;
  (d) determining the relative expression of the at least one mRNA biomarker in relation to the expression of a reference gene, wherein an increase in the expression level of the ANLN, HSD17B10, NUSAP1, SF1, SRD5A1, UBE2C, CYP17A1 and cofactors group, androgen controlled group, or any combination thereof in the patient sample relative to the expression level of the reference gene indicates an increased likelihood of progression free survival, overall survival, or both for said patient following treatment with AA, or wherein a decrease in the expression level of the multivariate panel group in the patient sample relative to the expression level of the reference gene indicates an increased likelihood of progression free survival for said patient following treatment with AA; and (e) treating said patient with a therapeutically effective amount of AA and prednisone.

As used herein, the term "patient" refers to any mammal having CRPC and whose sample can be analyzed with the disclosed methods. Thus, the disclosed methods are applicable to human and nonhuman subjects, although it is most preferably used for humans. In some embodiments, the patient sample is a human sample. In other embodiments, the patient sample is a nonhuman sample. "Patient" and "subject" are used interchangeably herein.

As used herein, the phrase "castration-resistant prostate cancer" (CRPC) refers to prostate cancer that is no longer responsive to castration treatment (reduction of available androgen/testosterone/DHT by chemical or surgical means) but exhibits a reliance upon hormones for androgen receptor activation.

Those skilled in the art know that abiraterone acetate (referred to herein as "AA") is a 17a-hydroxylase/C17,20-lyase (CYP17) inhibitor that blocks androgen synthesis in the testes, adrenal gland, and prostate tumor.

As used herein, the term "survival" refers to radiographic progression free survival (rPFS), overall survival (OS), or a combination thereof. As used herein, the phrase "radiographic progression free survival" refers to the length of time during and after the treatment that the patient lives with CRPC, but wherein the CRPC does not get worse determined, for example, by monitoring lesions in bone, soft-tissue, or any combination thereof with x-ray, CT, MRI, or any combination thereof. As used herein, the phrase "overall survival" refers to the length of time from either the date of diagnosis of CRPC or the start of treatment that the patient remains alive, i.e. to death from any cause.

In some embodiments, the disclosed methods predict a likelihood of the length of time (during and after the treatment) that the patient will live with CRPC, but wherein the CRPC will not worsen. In other embodiments, the disclosed methods predict a likelihood of the length of time (from either the date of diagnosis of CRPC or the start of treatment) that the patient will remain alive. In yet other embodiments, the disclosed methods predict a likelihood of both.

As used herein, the phrase "at least one mRNA biomarker" refers to single mRNA biomarkers or mRNA biomarker groups (i.e. two or more associated biomarkers) which may be used as an indicator of patients having tumor subtypes that may respond better to therapy with AA and prednisone and/or that may be predictive of primary resistance (or response) to AA and prednisone in CRPC. Exemplary single mRNA biomarkers are listed in Table 1 and include, but are not limited to, ANLN, HSD17B10, NUSAP1, SF1, SRD5A1, and UBE2C. Exemplary mRNA biomarker groups are listed in Table 1 and include, but are not limited to, CYP17A1 and cofactors (CYB5A, CYP17A1, CYP3A5, DUSP5, HNF1A, NR0B1, and POR) group, androgen controlled group (AKR1C3, FKBP5, and PCNA), and multivariate panel (AR, CYP21A2/CYP21A1P, HLA-A, IGJ, KRT17, LCN2, and PCNA).

TABLE 1

Exemplary single mRNA biomarkers and mRNA biomarker groups

| mRNA Biomarker | Name | GenBank Accession No. |
|---|---|---|
| Single mRNA Biomarker | | |
| ANLN | Anillin, actin binding protein | NM_018685.2 |
| HSD17B10 | Hydroxysteroid (17-beta) dehydrogenase 10 | NM_001037811.2 |
| NUSAP1 | Nucleolar and spindle associated protein 1 | NM_001243142.1 |
| SF1 | Splicing factor 1 (SF1), transcript variant 6 | NM_001178030.1 |
| UBE2C | Ubiquitin-conjugating enzyme E2C | NM_001281741.1 |
| SRD5A1 | Steroid-5-alpha-reductase, alpha polypeptide 1 (3-oxo-5 alpha-steroid delta 4-dehydrogenase alpha 1) | NM_001047.2 |
| mRNA Biomarker Groups Androgen controlled | | |
| AKR1C3 | Aldo-keto reductase family 1, member C3 | NM_001253908.1 |
| FKBP5 | FK506 binding protein 5 | NM_001145775.1 |
| PCNA | Proliferating cell nuclear antigen | NM_002592.2 |
| CYP17A1 and Cofactors | | |
| CYP17A1 | Cytochrome P450, family 17, subfamily A | NM_000102.3 |
| CYB5A | Cytochrome b5 type A (microsomal) | NM_001914.3 |
| POR | P450 (cytochrome) oxidoreductase (POR) | NM_000941.2 |
| CYP3A5 | cytochrome P450, family 3, subfamily A, polypeptide 5 | NM_000777.3 |
| DUSP5 | Dual specificity phosphatase 5 | NM_004419.3 |
| HNF1A | Transcription factor 1, hepatic; LF-B1, hepatic nuclear factor | NM_000545.3 |
| NR0B1 | Nuclear receptor subfamily 0, group B, member 1 | NM_000475.4 |
| Multivariate panel group | | |
| AR | Androgen receptor | NM_000044.3 |
| CYP21A2; CYP21A1P | Cytochrome P450, family 21, subfamily A, polypeptide 2; Cytochrome P450, family 21, subfamily A, polypeptide 1 pseudogene | NM_000500.7 |
| HLA-A | Major histocompatibility complex, class I, A | NM_001242758.1 |
| IGJ | Immunoglobulin J polypeptide, linker protein for immunoglobulin alpha and mu polypeptides | NM_144646.3 |
| KRT17 | Keratin 17 | NM_000422.2 |
| LCN2 | Lipocalin 2 | NM_005564.3 |
| PCNA | Proliferating Cell Nuclear Antigen | NM_002592.2 |

Thus, in some embodiments, the "at least one mRNA biomarker" refers to one or more single mRNA biomarkers including, but not limited to, ANLN, HSD17B10, NUSAP1, SF1, SRD5A1, UBE2C, or any combination thereof. In other embodiments, the "at least one mRNA biomarker" refers to one or more mRNA biomarker groups including, but not limited to, CYP17A1 and cofactors group, androgen controlled group, multivariate panel, or any combination thereof. For example, in some aspects of the methods the CYP17A1 and cofactors group comprises CYB5A, CYP17A1, CYP3A5, DUSP5, HNF1A, NR0B1, and POR. In some aspects of the methods, the androgen controlled group comprises AKR1C3, FKBP5, and PCNA. In some aspects of the methods, the multivariate panel comprises AR, CYP21A2/CYP21A1P, HLA-A, IGJ, KRT17, LCN2, and PCNA. In yet other embodiments, the "at least one mRNA biomarker" refers to one or more single mRNA biomarkers in addition to one or more mRNA biomarker groups including, but not limited to, ANLN, HSD17B10, NUSAP1, SF1, SRD5A1, UBE2C, CYP17A1 and cofactors group, androgen controlled group, multivariate panel, or any combination thereof.

As used herein, the phrase "contacting cDNA . . . with a gene chip" refers to a procedure whereby cDNA derived from a patient's tumor sample is incubated with, or added to, a gene chip in order to evaluate gene expression.

In some embodiments, the gene chip comprises probes for at least one mRNA biomarker, and wherein the at least one mRNA biomarker comprises ANLN, HSD17B10, NUSAP1, SF1, SRD5A1, UBE2C, CYP17A1 and cofactors group, androgen controlled group, multivariate panel, or any combination thereof. In other embodiments, the gene chip consists essentially of probes for at least one mRNA biomarker, and wherein the at least one mRNA biomarker comprises ANLN, HSD17B10, NUSAP1, SF1, SRD5A1, UBE2C, CYP17A1 and cofactors group, androgen controlled group, multivariate panel or any combination thereof. In yet other embodiments, the gene chip consists of probes for at least one mRNA biomarker, and wherein the at least one mRNA biomarker comprises ANLN, HSD17B10, NUSAP1, SF1, SRD5A1, UBE2C, CYP17A1 and cofactors group, androgen controlled group, multivariate panel or any combination thereof.

Those skilled in the art know that numerous procedures are available for measuring an expression level of the at least one mRNA biomarker including, but not limited to, quantitative RT-PCR, microarray, RNA sequencing, Nanostring, or any combination thereof.

As used herein, "reference gene" refers to one or more housekeeping genes including, but not limited to, GAPDH, Hs99999905_m1, ACTB, Hs99999903_m1, or any combination thereof.

In some embodiments, the expression level of the reference gene comprises a geometric mean of housekeeping genes. In such embodiments, comparing the expression level of the at least one mRNA biomarker to an expression level of a reference gene can comprise comparing the level of expression of the at least one mRNA biomarker to the geometric mean of the housekeeping genes. For example, expression values of single mRNA biomarkers can be calculated using the comparative CT method as described in Schmittgen T D, Livak K J. *Analyzing real-time PCR data by the comparative CT method*. Nature Protocols. 2008; 3:1101-1108, which is incorporated herein. Briefly, a normalization factor can be calculated for each sample using a geometric mean of housekeeping genes. Relative expression values of all other transcripts can be quantified as the difference between the CT and the normalization factor. Transcript expression can then be calculated by the negation of the relative expression values to account for the inverse relationship between expression and CT (this is equivalent to the log 2 transform of 2^(-DeltaCT)).

In other embodiments, comparing the expression level of a biomarker group to an expression level of a reference gene can comprise genewise normalization and summarization of member genes in the biomarker group. For example, the expression level of a biomarker group can first be normalized using the comparative CT method as discussed above and a summarized score can be derived for the biomarker group by computing the median of z-scores (e.g. transformed values obtained by subtracting the mean expression from the expression in a sample, and dividing by the standard deviation of the expression) of member genes in the biomarker group.

In other embodiments, a multivariate panel of biomarkers can be derived using penalized regression of time to event data. A set of data can be used to specify model parameters and select informative biomarkers via cross-validation. For an individual with biomarker expression X, the risk of experiencing an event relative to the average patient is given by exp(Xβ), where β is the log hazard ratio defined based on the association of biomarker expression with time to event in the data used to define the model and exp is the exponential function. In this manner, each individual patient's relative risk can be predicted on the basis of biomarker expression. Relative risk can be evaluated as a continuous index of the probability that the patient will experience a survival event or it can be dichotomized to indicate low and high risk groups of patients.

In some embodiments, an increase in the expression level of the ANLN, HSD17B10, NUSAP1, SF1, SRD5A1, UBE2C, CYP17A1 and cofactors group, androgen controlled group, or any combination thereof in the patient sample relative to the expression level of the reference gene is indicative of increased rPFS, OS, or a combination thereof.

Provided herein are methods of predicting a likelihood of survival following treatment with AA in a patient having CRPC, the method comprising:

(a) contacting cDNA from a tumor sample of the patient obtained prior to treatment with AA with a gene chip, wherein said gene chip comprises probes for at least one mRNA biomarker, and wherein the at least one mRNA biomarker comprises ANLN, HSD17B10, NUSAP1, SF1, SRD5A1, UBE2C, CYP17A1 and cofactors group, androgen controlled group, or any combination thereof;

(b) measuring an expression level of the at least one mRNA biomarker;

(c) comparing the expression level of the at least one mRNA biomarker to an expression level of a reference gene, wherein an increase in the expression level of the ANLN, HSD17B10, NUSAP1, SF1, SRD5A1, UBE2C, CYP17A1 and cofactors group, androgen controlled group, or any combination thereof in the patient sample relative to the expression level of the reference gene indicates an increased likelihood of progression free survival, overall survival, or both for said patient following treatment with AA; and (d) treating said patient with a therapeutically effective amount of AA and prednisone.

In some embodiments, a decrease in the expression level of the multivariate panel group in the patient sample relative to the expression level of the reference gene indicates an increased likelihood of progression free survival for said patient following treatment with AA.

Provided herein are methods of predicting a likelihood of survival following treatment with AA in a patient having CRPC, the method comprising:

(a) contacting cDNA from a tumor sample of the patient obtained prior to treatment with AA with a gene chip, wherein said gene chip comprises probes for at least one mRNA biomarker, and wherein the at least one mRNA biomarker comprises multivariate panel group;

(b) measuring an expression level of the at least one mRNA biomarker;

(c) comparing the expression level of the at least one mRNA biomarker to an expression level of a reference gene, wherein a decrease in the expression level of the multivariate panel group in the patient sample relative to the expression level of the reference gene indicates an increased likelihood of progression free survival for said patient following treatment with AA; and (d) treating said patient with a therapeutically effective amount of AA and prednisone.

In some embodiments, an increase in the expression level of the ANLN, HSD17B10, NUSAP1, SF1, SRD5A1, UBE2C, CYP17A1 and cofactors group, or androgen controlled group in the patient sample relative to the expression level of the reference gene indicates an increased likelihood of progression free survival, overall survival, or both for said patient following treatment with AA, and a decrease in the expression level of the multivariate panel group in the patient sample relative to the expression level of the reference gene indicates an increased likelihood of progression free survival for said patient following treatment with AA.

In some embodiments, increased rPFS and/or OS is indicated by an increase or decrease in the expression level of the at least one mRNA biomarker relative to the median expression value of the at least one mRNA biomarker from a patient population. Exemplary median expression values are provided in Table 4, herein. In other embodiments, increased rPFS and/or OS is indicated by any level of increase in the expression of ANLN, HSD17B10, NUSAP1, SF1, SRD5A1, UBE2C, CYP17A1 and cofactors group, or androgen controlled group or a decrease in the expression level of the multivariate panel group relative to the reference gene. For example, and without intent to be limiting, the Hazard Ratios (HRs) exemplified in Table 3 indicate the strength of the association between the relative expression of the at least one mRNA biomarker and outcome (e.g. rPFS or OS). Therefore, a unit increase in the relative expression of ANLN, for example, reduces the hazard of rPFS event by 16 percent (i.e. 1−0.84=0.16). Because the expression values of the at least one mRNA biomarker were log 2 transformed, a unit of change equates to a 2-fold difference relative to the expression level of the reference gene.

Numerous procedures are known for isolating RNA from a tumor sample including, but not limited to, commercially available kits such as AllPrep DNA/RNA FFPE Kit from Qiagen and the Ambion Recoverall kit. Additionally, one skilled in the art would know how to synthesize cDNA from the isolated RNA, including, but not limited to, the use of Life Technologies High Capacity cDNA Reverse Transcription Kit.

As used herein, "treating" comprises administering to a patient a therapeutically effective dose of AA and prednisone such that the CRPC and/or the associated symptoms are reduced, ameliorated, alleviated, reversed, inhibited, prevented and/or eliminated. Treating also encompasses a reduction in severity and/or frequency of symptoms, elimination of symptoms and/or underlying cause, prevention of the occurrence of symptoms and/or their underlying cause, and improvement or remediation of damage caused by CRPC.

In some embodiments, AA (CB7630) and prednisone are co-administered. For example, AA and prednisone may be administered sequentially in either order or contemporaneously.

The "therapeutically effective dose of AA and prednisone" will be dependent on several factors including, but not limited to, stage and severity of the CRPC, as well as other factors relating to the health of the patient. Those skilled in the art would know how to determine the therapeutically effective dose.

In some embodiments, the patient exhibiting increased expression of the at least one mRNA biomarker may have nonmetastatic or early stage CRPC. In other embodiments, the patient exhibiting increased expression of the at least one mRNA biomarker may have metastatic or late stage CRPC.

EXAMPLES

Study Design

COU-AA-302 is a Phase 3, multinational, randomized, double-blind, placebo-controlled study comparing the efficacy and safety of AA and prednisone (AA+P) to placebo and prednisone (Placebo+P) in medically or surgically castrated asymptomatic or mildly symptomatic men with mCRPC who have not received cytotoxic chemotherapy. Patients were assigned in a 1:1 ratio to receive either AA+P or Placebo+P and were stratified based on ECOG performance status of 0 or 1, as discussed in *Clinical Study Protocol: A Phase* 3 *Randomized, Double-blind, Placebo-controlled Study of Abiraterone Acetate (CB7630) Plus Prednisone in Asymptomatic or Mildly Symptomatic Subjects with Metastatic Castration Resistant Prostate Cancer*. Protocol COU-AA-302; EudraCT No. 2008-008004-41; 9 Jul. 2012.

All subjects in Study COU-AA-302, regardless of treatment group, received concurrent prednisone. See *Clinical Study Report: CSR COU-AA*-302 2012. *A Phase* 3, *Randomized, Double-Blind, Placebo-Controlled Study of Abiraterone Acetate Plus Prednisone in Asymptomatic or Mildly Symptomatic Subjects With Metastatic Castration-Resistant Prostate Cancer*. Issue Date: 26 Oct. 2012. Subjects who received AA+P are referred to herein as the "AA group" and in tables as "AA." Subjects who received Placebo+P are referred to herein as the "Placebo group" and in tables as "Placebo." Additional study related details can be obtained from the COU-AA-302 clinical study protocol or clinical study report.

Biomarker Sample Collection and Processing

Formalin fixed paraffin embedded (FFPE) tumor samples from 258 subjects who optionally consented for RNA analysis were collected and shipped to the central laboratory (Covance, Ind.) for RNA analysis. FFPE samples from 152 subjects had sufficient RNA for TaqMan® Low Density Array (TLDA) analysis. Samples from the other 106 subjects were excluded either due to lack of tumor or low RNA yield. Of the 152 samples evaluated by TLDA, samples from 42 subjects were excluded from data analysis due to technical failures (no detectable gene expression or batch effects induced by microdissection of samples with low tumor content or low RNA input mass [<250 ng of total RNA]). The remaining evaluable samples from 110 subjects (Biomarker population) who were part of the ITT population (10%) and who had drug exposure with clinical data for at least one of the efficacy endpoints (rPFS, OS) were included in the analysis. Samples from these subjects were included in the mRNA analysis using the TaqMan® array microfluidic cards.

Ninety-six mRNAs were selected for gene expression profiling, including CYP17A1 and cofactors (CYP17, P450 reductase, and cytochrome b5) along with AR and its splice variants (AR full length, AR V7, and AR567ES). Also included in the analysis were genes representing major biological pathways including androgen signaling, proliferation, cell growth, immune response, and steroidogenic genes.

Methods for Sample Analysis
RNA Extraction

The RNA from FFPE samples was extracted by the central laboratory (Covance Genomics Laboratory, Seattle, Wash.) initially using the AllPrep DNA/RNA FFPE Kit from Qiagen as per manufacturer's instructions. To improve the yield of RNA in samples that failed extraction procedures due to the low RNA yield, Ambion Recoverall kit was used for remaining samples. RNA samples were treated with DNase according to manufacturer's recommendation and RNA quantity was measured via RiboGreen.

cDNA Synthesis, Pre-Amplification, and Microarray cDNA synthesis was performed using Life Technologies High Capacity cDNA Reverse Transcription Kit with RNase Inhibitor (Catalog Number 4374967) according to the vendor's protocol with the following minor modification: a 30 ul reaction volume was used in place of 20 ul. Total RNA of 250 ng was used for the cDNA synthesis with the exception of a subset of samples with low RNA yield (150 ng of total RNA was used), but these samples were subsequently excluded from statistical analysis due to batch effect.

Preamplification was performed using Life Technologies TaqMan® PreAmp Master Mix Kit (Catalog Number 4384267) according to the vendor's protocol. TaqMan® Array Microfluidic Cards from Applied Biosystems were used for RNA analysis and run according to the vendor's protocol. The card was run on an ABI 7900 HT System.

TABLE 2

DNA sequences of primers used to assay the expression of biomarkers

| Biomarker | Primer Sequence | SEQ ID NO: | Region* |
|---|---|---|---|
| mRNA Biomarker | | | |
| ANLN | CCAAGGCTATTACTCCAAAGCGACTC CTCACATCTATAACCACAAAAAGCAA CATTCATTCTTCAGTCATGG | 1 | 2909-2980 |
| HSD17B10 | GACCTCTGAGAAGGATGTGCAAACAG CTCTGGCTCTAGCAAAAGGAAAGTTT GGCCGTGTGGATGTAGCTGTCAACT | 2 | 226-302 |
| NUSAP1 | GTCAGGTTTTCAGCTGCTACTAAAGA TAATGAGCATAAGCGTTCACTGACCA AGACTCCAGCCAGAAAGTCTGCACAT GTGACCGTGT | 3 | 1102-1189 |
| SF1 | TCCCCTTCCCCTGAGCCCATCTACAA TAGCGAGGGGAAGCGGCTTAACACCC GAGAGTTCCGCACCCGCAAAAAGCTG GAAGAGGAGCGGCACAACCTCATCA CAGAGATGGTTGCAC | 4 | 687-804 |
| UBE2C | TTAAGAAGTACCTGCAAGAAACCTAC TCAAAGCAGGTCACCAGCCAGGAGCC CTGACCCAGGCT | 5 | 464-528 |

TABLE 2-continued

DNA sequences of primers used to assay the expression of biomarkers

| Biomarker | Primer Sequence | SEQ ID NO: | Region* |
|---|---|---|---|
| SRD5A1 | CGGTGCTTAATTTACCCATTTCTGAT GCGAGGAGGAAAGCCTATGCCACTGT TGGCGTGTACAATGGCGATTATGT | 6 | 482-557 |
| mRNA Bio-marker Groups | | | |
| Androgen controlled | | | |
| AKR1C3 | TTGCTAGCCACCCTAATTATCCATAT TCAGATGAATATTAACATGGAGGGCT TTGCCTGATGTCTACCAGAAGCCCTG TGTGTGGATGGTGACGCAGAGGACGT CTCTATGCC | 7 | 978-1090 |
| FKBP5 | CAAGGAAGAGGCCAATAAAGCAATG GGCAAGAAGACTTCAGAAGGGGTCA CTAATGAAAAAGGAACAGACAGTCA AGCAATG | 8 | 1579-1660 |
| PCNA | AACCAGGAGAAAGTTTCAGACTATGA AATGAAGTTGATGGATTTAGATGTTG AACAACTTGGAATTCCAGAACAGGAG TACAGCTGTGTAGTAAAGATGCCTTC TGGTGAATTTGCACGTATATGCCGAG ATCTCAGCC | 9 | 558-696 |
| CYP17A1 and Cofactors | | | |
| CYP17A1 | CAGCATCGGTGAGTTTGCTGTGGACA AGGGCACAGAAGTTATCATCAATCTG TGGGCGCTGCATCACAATGAG | 10 | 1309-1381 |
| CYB5A | TGACAGACCAAAGTTAAACAAGCCTC CGGAACCTTAAAGGCGGTGTTTCAAG GAAACTCTTATCACTACTATTGATTC TAGTTCCAGTTGGTGGACCAACTGGG TGATCCCTGCCATCTCTGCAGTGGCC GTCGCCTTGATGTAT | 11 | 402-546 |
| POR | GCCGACCTGAGCAGCCTGCCAGAGAT CGACAACGCCCTGGTGGTTTTCTGCA TGGCCACCTACGGTGAGGGAGACCCC ACCGACAATGCCCAGGACTTCTACGA CTGGCTGCAGG | 12 | 449-563 |
| CYP3A5 | GGGGAACGTATGAAGGTCAACTCCCT GTGCTGGCCATCACAGATCCCGACGT GATCAGAACAGTGCTAGTGAAAGAAT GTTAT | 13 | 317-399 |
| DUSP5 | AGGGGGATATGAGACTTTCTACTCGG AATATCCTGAGTGTTGCGTGGATGTA AAACCCATTTCACAAGAGAAGATTGA GAGTGAGAGAGCCCTCATCAGCCAGT GTGG | 14 | 633-740 |
| HNF1 | CACCCATGCAGGGCAGGGAGGGCTG ATTGAAGAGCCCACAGGTGATGAGCT ACCAACCAAGAAGGGGCGGAGGAAC CGTTTCAAGTGGGGCCCAGCA | 15 | 554-650 |
| NR0B1 | ACCCGGACGTGCCGGGCCTGCAGTGC GTGAAGTACATTCAGGGACTCCAGTG GGGAACTCAGCAAATACTCAGTGAAC ACACCAGGATGACGCACCAAGGGCC CCATGACAGATTCATCGAACTTAATA GTACCCTTTTC CTGCTG | 16 | 1178-1323 |

TABLE 2-continued

DNA sequences of primers used to assay the expression of biomarkers

| Biomarker | Primer Sequence | SEQ ID NO: | Region* |
|---|---|---|---|
| Multivariate panel group | | | |
| AR | GCTTCCGCAACTTACACGTGGACGAC CAGATGGCTGTCATTCAGTACTCCTG GATGGGGCTCATGGTGTTTG | 17 | 3289-3360 |
| CYP21A2; CYP21A1P | GTGAGCGCATGAGAGCCCAGCCCGGC ACCCCTGTGGCCATTGAGGAGGAATT CTCTCTCCTCACCTGCAGCATCATCT GTTACCTCACCTTCGGAGACAAGATC AAGGACGACAACTTAAT | 18 | 550-671 |
| HLA-A | CTGCAAGCAGTGACAGTGCCCAGGGC TCTGATGTGTCTCTCACAGCTTGTAA AGTGTGAGACAGCTGCCT | 19 | 1034-1104 |
| IGJ | TGTTCCTCTGAACAACAGGGAGAATA TCTCTGATCCCACCTCACCATTGAGA ACCAGATTTGTGTACCATTTGTCTGA CCTCTGTAAAAAATGTGATCCTACAG AAGTGGAGCTGGA | 20 | 330-447 |
| KRT17 | GAACAAGATCCTCACAGCCACCGTGG ACAATGCCAACATCCTGCTACAGATT GACAATGCCCGTCTGGCTGCTGATGA CTTCCGCACCAAGTT | 21 | 547-640 |
| LCN | TCCCAATCGACCAGTGTATCGACGGC TGAGTGCACAGGTGCCGCCAGCTGCC GCACCAGCC | 22 | 642-703 |
| PCNA | AACCAGGAGAAAGTTTCAGACTATGA AATGAAGTTGATGGATTTAGATGTTG AACAACTTGGAATTCCAGAACAGGAG TACAGCTGTGTAGTAAAGATGCCTTC TGGTGAATTTGCACGTATATGCCGAG ATCTCAGC | 23 | 558-696 |

*The region indicates the bases in the target transcript that comprise the primer region.

Data Normalization

Raw CT values were filtered to remove values greater than 30. Quadruple replicate CT values were summarized using the geometric mean. Expression values were calculated using the comparative CT method as described in Schmittgen T D, Livak K J. Analyzing real-time PCR data by the comparative Ct method. Nature Protocols. 2008; 3:1101-1108. Briefly, a normalization factor was calculated for each sample using the geometric mean of housekeeping genes (ACTB and GAPDH). Relative expression values of all other transcripts were quantified as the difference between CT and the normalization factor. Transcript expression was calculated by the negation of the relative expression values to account for the inverse relationship between expression and CT. This is equivalent to the log 2 transform of $2^{-DeltaCT}$.

Statistical Analysis

All statistical tests were interpreted at 5% significance levels (two-sided). For determination of specificity of biomarker association with clinical endpoints in AA group, a $P<0.05$ in the AA group and a $P \geq 0.2$ in the placebo group is required. Demographics and baseline characteristics were compared between the biomarker population and the ITT population using ANOVA (continuous variables) or Chi-Square (categorical variables) tests.

Biomarker data received from the central laboratory was processed in the following order:
  Four samples with below lower limit of quantification (LLOQ) for all biomarkers were excluded.
  Seven biomarkers for which at least 95% of the sample data were missing or below LLOQ were also excluded.
  For subjects with duplicate samples, which were generated using the same extraction methodology, laser capture microdissection (LCM) methodology, and RNA input mass, the average value was used.
  Results below LLOQ for a biomarker were imputed by half of the minimum of all available values for the same biomarker. All biomarker values were then log 2-transformed.
  For analysis of biomarker groups, the median of normalized values from all biomarkers in a biomarker group was used to determine the composite score for each subject by first calculating z-score for each biomarker's imputed and log 2-transformed value across all subjects using (Biomarker value−mean across all subjects)/ (standard deviation across all subjects) and then summarizing the z-scores of all genes in each group by the median value to generate a biomarker group composite score.
  Association of these data with clinical endpoints (rPFS by Independent Review (IND), rPFS by Investigative Review (INV), and OS) were analyzed as follows:
  Cox regression was conducted as the main analysis method with baseline ECOG score (randomization stratification factor) and each biomarker value (continuous) or composite score for biomarker group (continuous) in the model for each treatment group and for the total biomarker population.
  To correct for RNA extraction method, Cox regression was conducted with baseline ECOG score, RNA extraction method (Qiagen AllPrep or Ambion RecoverAll) and each biomarker value (continuous) or composite score for biomarker group (continuous) in the model for each treatment group and for the total biomarker population.
  Dichotomized biomarker data by median ($\geq$median or <median) were used in Cox regression that was conducted for each treatment group and for the total biomarker population.
  Treatment group comparison was performed in biomarker subpopulation defined by dichotomized biomarker data based on median using Cox regression.
  Relevant p values (type III), HR, and 95% confidence intervals are presented for each association in the data tables.
  For biomarkers with the highest significance (consistent association with multiple clinical endpoints), the Kaplan-Meier method was used to estimate the distribution of rPFS and OS.

Biomarker Results

Demographics and Baseline Characteristics

The biomarker population was generally representative of the overall ITT population in the COU-AA-302 study (Data not shown). However, the biomarker population had a higher frequency of subjects with previous surgeries and included a higher percentage of subjects outside of North America. No statistically significant differences for other demographic and baseline characteristics were observed.

Frequency of Gene Expression

Of the 94 mRNA biomarkers tested, 87 non-housekeeping mRNAs had expression in at least 5% of the samples. The number of tumors with detectable expression values varied for each gene (Data not shown). Notably, AR full length was detected in all tumors tested, while AR V7 was detectable in 65.5% of samples and AR567ES expression was not observed in any of the subjects (Data not shown). The frequency of CYP17 detectable expression was 30.9% (Data not shown).

Association Analysis of Biomarkers with rPFS (Independent Review)—Single mRNA Biomarker Association analysis of single mRNA biomarker expression values with rPFS (IND) was evaluated using Cox regression within each treatment group or in the treatment groups combined. Baseline ECOG scores and the randomization stratification factor were included in the model. The biomarkers that showed consistent association with rPFS by IND and other clinical endpoints are summarized in Table 3.

Out of 94 mRNA biomarkers examined, eight biomarkers showed significant association with rPFS (IND) in the AA group ($p<0.05$), but not in the Placebo group ($p \geq 0.2$), indicating that the expression of these biomarkers may be predictive of AA efficacy (Data not shown). These biomarkers included: CYP17 cofactors (HNF1A); AR regulated genes (KLK3), proliferation markers (ANLN, NUSAP1, UBE2C); an enzyme in the "backdoor" synthesis of dihydrotestosterone (DHT), HSD17B10; an enzyme in the conversion pathway of C19 steroids, SRD5A1; and pre-mRNA splicing factor SF1. After correcting for the RNA extraction methodology in a multivariate Cox regression model, ANLN (HR=0.86; p=0.0413), HSD17B10 (HR=0.78; p=0.0396), NUSAP1 (HR=0.78; p=0.0272), and SRD5A1 (HR=0.79; p=0.0360) remained significantly associated with rPFS (IND) in the AA group and UBE2C showed a trend of association with rPFS (IND) in the AA group (HR=0.88; p=0.0584).

Association of biomarkers with rPFS (IND) was also evaluated using Cox regression with biomarker expression dichotomized into binary variables using the median expression as a cutpoint. The results were similar to the analysis done with treating biomarker data as continuous variables (Data not shown).

Association Analysis of Biomarkers with rPFS (Independent Review)—mRNA Biomarker Group Association of biomarker composite scores with rPFS (IND) was evaluated by Cox regression stratified by ECOG scores. One biomarker group, "androgen controlled genes" that included AKR1C3, FKBP5, and PCNA, was significantly associated with rPFS (IND) in the AA group, but not in the Placebo group before (HR=0.57 [0.37, 0.88]; p=0.0115) and after (HR=0.63 [0.39,0.99], p=0.0467) correcting for RNA methodology, suggesting an association with efficacy to AA treatment. Additionally, CYP17A1 and cofactors group (CYB5A, CYP17A1, CYP3A5, DUSP5, HNF1A, NR0B1, POR; HR=0.43 [0.21,0.89]; p=0.0224) also showed significant association with rPFS (IND) in the AA group but not in the Placebo group. (See Table 3)

Association Analysis of Biomarkers with rPFS (Investigator Review)—Single mRNA Biomarker Association of single mRNA biomarkers with rPFS (INV) was evaluated using the same method as for rPFS (IND). Twelve biomarkers were associated with rPFS in the AA group but not in the Placebo group (Data not shown). Of these, five biomarkers—HSD17B10, SF1, UBE2C, NUSAP1, and SRD5A1—were associated with both rPFS (IND) and rPFS (INV). (See Table 3).

Association Analysis of Biomarkers with rPFS (Investigator Review)—mRNA Biomarker Group Association of biomarker groups with rPFS (INV) were evaluated using the same method as for rPFS (IND). Four biomarker groups were associated with rPFS in the AA group, but not in the Placebo group (Data not shown). Of these, two biomarker groups, androgen controlled genes (HR=0.58; p=0.0220) and proliferation pathway module (HR=0.63; p=0.0133) were associated with both rPFS (IND) and rPFS (INV).

Association Analysis of Biomarkers with OS—Single mRNA Biomarker

Association of single mRNA biomarkers with OS was evaluated using the same method as for rPFS (IND). Eleven biomarkers were associated with OS in the AA group, but not in the Placebo group (Data not shown). Of these, SF1 was associated with both rPFS (rPFS IND: HR=0.82; p=0.0214; rPFS INV: HR=0.78; p=0.0095) and OS (HR=0.67 [0.50,0.89]; p=0.0066).

Association Analysis of Biomarkers with OS—mRNA Biomarker Group

Association of biomarker groups with OS was evaluated using the same method as for rPFS (IND). Five biomarker groups were associated with OS in the AA group, but not in the Placebo group (Data not shown). Of these, two biomarker groups, androgen controlled genes (rPFS IND: HR=0.57; p=0.0115; OS: HR=0.31; p=0.0037) and CYP17A1 and cofactors (rPFS IND: HR=0.43; p=0.0224; OS: HR=0.20; p=0.0156) were associated with both rPFS and OS.

TABLE 3

Association of mRNA biomarkers with rPFS(IND) and rPFS(INV) within each treatment group

| | | AA | | Placebo | |
|---|---|---|---|---|---|
| | Endpoint | P value | HR | P value | HR |
| mRNA Biomarker | | | | | |
| MRNA10(ANLN-Hs01122612_m1) | rPFS (IND) | 0.014 | 0.84 (0.72, 0.96) | 0.6693 | 0.97 (0.82, 1.13) |
| | rPFS (INV) | 0.0032 | 0.80 (0.69, 0.93) | 0.3146 | 0.93 (0.80, 1.07) |
| MRNA40(HSD17B10-Hs00189576_m1) | rPFS (IND) | 0.0343 | 0.78 (0.62, 0.98) | 0.3271 | 0.90 (0.73, 1.11) |
| | rPFS (INV) | 0.0124 | 0.76 (0.62, 0.94) | 0.3911 | 0.92 (0.75, 1.12) |
| MRNA70(NUSAP1-Hs01006195_m1) | rPFS (IND) | 0.0491 | 0.82 (0.67, 1.00) | 0.7724 | 1.03 (0.85, 1.25) |
| | rPFS (INV) | 0.0119 | 0.78 (0.64, 0.95) | 0.2736 | 0.91 (0.76, 1.08) |
| MRNA81(SF1-Hs00190309_m1) | rPFS (IND) | 0.0214 | 0.82 (0.69, 0.97) | 0.6734 | 0.97 (0.82, 1.13) |
| | rPFS (INV) | 0.0095 | 0.78 (0.64, 0.94) | 0.9223 | 1.01 (0.86, 1.18) |

TABLE 3-continued

Association of mRNA biomarkers with rPFS(IND)
and rPFS(INV) within each treatment group

| | | AA | | Placebo | |
|---|---|---|---|---|---|
| | Endpoint | P value | HR | P value | HR |
| MRNA82(SRD5A1-Hs00971643_g1) | rPFS (IND) | 0.0337 | 0.80 (0.65, 0.98) | 0.228 | 0.87 (0.70, 1.09) |
| | rPFS (INV) | 0.0468 | 0.83 (0.68, 1.00) | 0.3152 | 0.90 (0.74, 1.10) |
| MRNA92(UBE2C-Hs00964100_g1) | rPFS (IND) | 0.0213 | 0.85 (0.74, 0.98) | 0.9156 | 1.01 (0.85, 1.20) |
| | rPFS (INV) | 0.0022 | 0.81 (0.71, 0.93) | 0.2194 | 0.91 (0.78, 1.06) |
| mRNA biomarker groups | | | | | |
| GP03(CYP17A1 and cofactors) | rPFS (IND) | 0.0224 | 0.43 (0.21, 0.89) | 0.8164 | 1.07 (0.59, 1.94) |
| | rPFS (INV) | 0.3002 | 0.71 (0.37, 1.36) | 0.9498 | 1.02 (0.56, 1.84) |
| GP08(androgen controlled) | rPFS (IND) | 0.0115 | 0.57 (0.37, 0.88) | 0.201 | 1.26 (0.88, 1.81) |
| | rPFS (INV) | 0.022 | 0.58 (0.37, 0.92) | 0.6608 | 1.08 (0.78, 1.49) |

Biomarkers or biomarker groups associated with rPFS in the AA group (P < 0.05) but not in the placebo arm (P >= 0.2). Association of biomarker expression with rPFS in AA or placebo group is determined using cox regression. P-value indicates the significance of the association. Hazard Ratio (HR) indicates the magnitude of the association Summary Statistics Summary statistics including the number of observations (N), the average and standard deviation of expression, the median expression, first and third quartiles and minimum and maximum expression level for each biomarker are shown in Table 4.

TABLE 4

Summary statistics of mRNA biomarkers

| | N | Mean (sd) | Median | Q1, Q3 | Min, Max |
|---|---|---|---|---|---|
| mRNA Biomarker | | | | | |
| MRNA10(ANLN-Hs01122612_m1) | 110 | −0.06 (2.13) | 0.05 | −1.76, 1.62 | −5.75, 5.22 |
| MRNA40(HSD17B10-Hs00189576_m1) | 110 | 0.91 (1.57) | 1.25 | −0.17, 2.03 | −3.08, 4.26 |
| MRNA70(NUSAP1-Hs01006195_m1) | 110 | −2.28 (1.75) | −2.18 | −3.46, −0.89 | −6.80, 1.80 |
| MRNA81(SF1-Hs00190309_m1) | 110 | −2.11 (1.78) | −1.82 | −3.02, −0.93 | −6.85, 0.99 |
| MRNA82(SRD5A1-Hs00971643_g1) | 110 | −0.46 (1.84) | −0.36 | −1.59, 0.69 | −4.99, 6.99 |
| MRNA92(UBE2C-Hs00964100_g1) | 110 | −0.11 (2.17) | 0.24 | −2.01, 1.49 | −5.82, 4.78 |
| mRNA Biomarker Groups | | | | | |
| GP03(CYP17A1 and cofactors) | 110 | −0.09 (0.55) | −0.13 | −0.49, 0.18 | −1.23, 1.78 |
| GP08(androgen controlled) | 110 | 0.01 (0.81) | 0.24 | −0.39, 0.58 | −1.54, 1.79 |

Coefficients were derived from Cox regression model of biomarker expression and baseline ECOG status against time to radiographic progression free survival. Table 5 provides model parameters for each marker. Using these values, expression of the biomarker and baseline ECOG status can be translated into relative risk of rPFS.

TABLE 5

Regression coefficients for survival models

| Marker | Marker. Coef | BLECOG. Coef |
|---|---|---|
| GP03(CYP17A1 and cofactors) | −0.836 | −1.379 |
| GP08(androgen controlled) | −0.562 | −1.545 |
| MRNA10(ANLN-Hs01122612_m1) | −0.180 | −1.561 |
| MRNA40(HSD17B10-Hs00189576_m1) | −0.249 | −1.536 |
| MRNA70(NUSAP1-Hs01006195_m1) | −0.203 | −1.605 |
| MRNA81(SF1-Hs00190309_m1) | −0.204 | −1.559 |
| MRNA82(SRD5A1-Hs00971643_g1) | −0.224 | −1.596 |
| MRNA92(UBE2C-Hs00964100_g1) | −0.161 | −1.601 |

Optimization and Validation of Multivariate AA Response Biomarkers

A multivariate biomarker panel was identified using penalized regression to define a classifier that predicts radiographic progression free survival. The model was defined using an elastic net approach for feature selection and model specification. Data was separated into training and testing sets using a 70%-30% split. Within the training data, 10-fold cross-validation was used to define model parameters. Elastic net models have two parameters: alpha and lambda. Alpha is the elastic net penalty and determines the specific mixture of penalties that will be applied to limit complexity of the model. Lambda is the regularization penalty which determines the magnitude of the parameter used to limit complexity. After optimizing alpha and lambda using cross-validation, the values were used to define the cox regression model on the training data. The model is used to predict the relative risk of progression free-survival for all subjects in the training set. Then, time-dependent ROC analysis was used to determine the predictive power of the model and dichotomize the relative risk into two groups associated with low and high risk at the timepoint at which 90% of subjects with radiographic progression had observed recurrence of disease (t=20.48 months). This model, consisting of regression coefficients, timepoint and cutoff to discriminate between low and high risk, was applied to predict the relative risk of subjects in the independent test data and evaluate the predictive power and association with time to event of the classifier. This evaluation is repeated on the placebo data to confirm that the classifier is predictive of response to Abiraterone and not prognostic of outcome independent of treatment. Features used in the model building process included all single gene markers detected in greater than 50% of samples to exclude low expressing genes. The model was optimized to alpha=0.5 and lambda=0.209. Using these parameters, the optimized survival models were defined as described in Table 6.

TABLE 6

Optimized multivariate model based on expression of all single gene markers measured in >50% of subjects.

| Marker | Beta * |
|---|---|
| MRNA12(AR-Hs00171172_m1) | 0.226 |
| MRNA26(CYP21A2; CYP21A1P-Hs00365734_g1) | 0.062 |
| MRNA37(HLA-A-Hs01058806_g1) | 0.03 |
| MRNA50(IGJ-Hs00376160_m1) | 0.18 |
| MRNA57(KRT17-Hs01588578_m1) | 0.02 |
| MRNA59(LCN2-Hs01008571_m1) | 0.039 |
| MRNA71(PCNA-Hs00427214_g1) | 0.241 |

* Beta indicates the optimized regression coefficient for the associated marker.

Table 7 lists the predictive metrics which describe the performance of these models on the independent test and placebo group data.

TABLE 7

Predictive metrics of optimized multivariate model based on expression of all single gene markers measure in >50% of subjects.

| Data | Timepoint | KM | AUC |
|---|---|---|---|
| Test | 20.48134 | 0.474 | 0.778 |
| Placebo | 20.48134 | 0.262 | 0.627 |

Data indicates the dataset used i.e. independent test set or placebo data.
KM indicates the Kaplan-Meier survival estimate at time t.
AUC indicates the area under the ROC curve at time t.

Table 8 lists the statistics describing the association between classifier predictions and time to radiographic progression free survival.

TABLE 8

Association of predictive model with time to radiographic progression free survival

| Data | Cutpoint | Timepoint | Risk | Event/Total (Perc) | Median (95CI) | HR (95CI) | P (Cox) | P (KM) |
|---|---|---|---|---|---|---|---|---|
| Test | 0.9977 | 20.4813 | Low | 6/15 (40.0) | — (13.8, —) | — | — | — |
|  |  |  | High | 4/4 (100.0) | 8.2 (1.8, —) | 6.25 (1.54, 25.34) | 0.0104 | 0.0035 |
| Placebo | 0.9977 | 20.4813 | Low | 29/43 (67.4) | 11.0 (8.3, 13.8) | — | — | — |
|  |  |  | High | 3/5 (60.0) | 8.3 (1.7, —) | 0.97 (0.30, 3.20) | 0.9654 | 0.9652 |

What is claimed:

1. A method of treating castration-resistant prostate cancer (CRPC) in a human, the method comprising administering abiraterone acetate and prednisone to a human who has CRPC and who has an increased level of expression of an androgen controlled group relative to an expression level of at least one housekeeping gene, the increased level of expression of the androgen controlled group relative to the expression level of the at least one housekeeping gene being determined by:
   a) obtaining a tumor sample from said human;
   b) isolating RNA from the tumor sample;
   c) synthesizing cDNA from the RNA;
   d) measuring the threshold cycle (CT) of single mRNA biomarkers in the androgen controlled group in said sample using real-time PCR (RT-PCR), wherein the single mRNA biomarkers in the androgen controlled group are aldo-keto reductase family 1 member C3 (AKR1C3), FK506 binding protein 5 (FKBP5), and proliferating cell nuclear antigen (PCNA);
   e) determining a normalization factor for said sample by calculating a geometric mean of the at least one housekeeping gene in said sample;
   f) quantifying a relative expression value for each of the single mRNA biomarkers in the androgen controlled group by calculating the difference between the CT of each of the single mRNA biomarkers in the androgen controlled group from step (d) and the normalization factor from step (e);
   g) calculating a transcript expression level by negating the relative expression value of each of the single mRNA biomarkers in the androgen controlled group from step (f);
   h) calculating a z-score for each of the single mRNA biomarkers by:
      (1) calculating a mean transcript expression level for each single mRNA biomarker by averaging a transcript expression level for each single mRNA biomarker from tumor samples obtained from a population of male subjects having CRPC;
      (2) calculating a standard deviation of the transcript expression level for each single mRNA biomarker from said tumor samples obtained from said population of male subjects having CRPC; and
      (3) subtracting the mean transcript expression level from step h(1) from the transcript expression level of step (g) and dividing by the standard deviation of the transcript expression level from step h(2);
   i) deriving a summarized score for the androgen controlled group by computing a median of the z-scores of all of the single mRNA biomarkers from step (h); and
   j) based on the summarized score for the androgen controlled group, determining that the level of expression of the androgen controlled group is increased relative to the expression level of the at least one housekeeping gene.

2. The method of claim 1, wherein the human has non-metastatic castration-resistant prostate cancer.

3. The method of claim 1, wherein the at least one housekeeping gene is glyceraldehyde 3-phosphate dehydrogenase (GAPDH), beta actin (ACTB), or any combination thereof.

4. The method of claim 1, comprising two or more housekeeping genes.

5. The method of claim 3, wherein the human has not received cytotoxic chemotherapy.

* * * * *

SEQUENCE LISTING

<160> NUMBER OF SEQ ID NOS: 23

<210> SEQ ID NO 1
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccaaggctat tactccaaag cgactcctca catctataac cacaaaaagc aacattcatt      60
cttcagtcat gg                                                         72

<210> SEQ ID NO 2
<211> LENGTH: 77
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gacctctgag aaggatgtgc aaacagctct ggctctagca aaaggaaagt ttggccgtgt      60
ggatgtagct gtcaact                                                    77

```
<210> SEQ ID NO 3
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gtcaggtttt cagctgctac taaagataat gagcataagc gttcactgac caagactcca    60
gccagaaagt ctgcacatgt gaccgtgt                                       88

<210> SEQ ID NO 4
<211> LENGTH: 118
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tccccttccc ctgagcccat ctacaatagc gaggggaagc ggcttaacac ccgagagttc    60
cgcacccgca aaagctgga agaggagcgg cacaacctca tcacagagat ggttgcac     118

<210> SEQ ID NO 5
<211> LENGTH: 65
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttaagaagta cctgcaagaa acctactcaa agcaggtcac cagccaggag ccctgaccca    60
ggctg                                                                65

<210> SEQ ID NO 6
<211> LENGTH: 76
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cggtgcttaa tttacccatt tctgatgcga ggaggaaagc ctatgccact gttggcgtgt    60
acaatggcga ttatgt                                                    76

<210> SEQ ID NO 7
<211> LENGTH: 113
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttgctagcca ccctaattat ccatattcag atgaatatta acatggaggg ctttgcctga    60
tgtctaccag aagccctgtg tgtggatggt gacgcagagg acgtctctat gcc          113

<210> SEQ ID NO 8
<211> LENGTH: 82
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 8
caaggaagag gccaataaag caatgggcaa gaagacttca gaagggtca ctaatgaaaa        60 aggaacagac agtcaagcaa tg                                               82

<210> SEQ ID NO 9
<211> LENGTH: 139
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaccaggaga aagtttcaga ctatgaaatg aagttgatgg atttagatgt tgaacaactt       60
ggaattccag aacaggagta cagctgtgta gtaaagatgc cttctggtga atttgcacgt     120
atatgccgag atctcagcc                                                  139

<210> SEQ ID NO 10
<211> LENGTH: 73
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cagcatcggt gagtttgctg tggacaaggg cacagaagtt atcatcaatc tgtgggcgct       60
gcatcacaat gag                                                         73

<210> SEQ ID NO 11
<211> LENGTH: 145
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgacagacca aagttaaaca agcctccgga accttaaagg cggtgtttca aggaaactct       60
tatcactact attgattcta gttccagttg gtggaccaac tgggtgatcc ctgccatctc     120
tgcagtggcc gtcgccttga tgtat                                           145

<210> SEQ ID NO 12
<211> LENGTH: 115
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gccgacctga gcagcctgcc agagatcgac aacgccctgg tggttttctg catggccacc       60
tacggtgagg gagaccccac cgacaatgcc caggacttct acgactggct gcagg          115

<210> SEQ ID NO 13
<211> LENGTH: 83
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 13
ggggaacgta tgaaggtcaa ctccctgtgc tggccatcac agatcccgac gtgatcagaa      60
cagtgctagt gaaagaatgt tat                                             83

<210> SEQ ID NO 14
<211> LENGTH: 108
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14 aggggggatat gagactttct actcggaata tcctgagtgt tgcgtggatg taaaacccat    60
ttcacaagag aagattgaga gtgagagagc cctcatcagc cagtgtgg                  108

<210> SEQ ID NO 15
<211> LENGTH: 97
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cacccatgca gggcagggag ggctgattga agagcccaca ggtgatgagc taccaaccaa     60 gaagggggcgg aggaaccgtt tcaagtgggg cccagca                             97

<210> SEQ ID NO 16
<211> LENGTH: 146
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
acccggacgt gccgggcctg cagtgcgtga agtacattca gggactccag tggggaactc     60
agcaaatact cagtgaacac accaggatga cgcaccaagg gccccatgac agattcatcg    120
aacttaatag tacccttttc ctgctg                                         146

<210> SEQ ID NO 17
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcttccgcaa cttacacgtg gacgaccaga tggctgtcat tcagtactcc tggatggggc     60
tcatggtgtt tg                                                         72

<210> SEQ ID NO 18
<211> LENGTH: 121
<212> TYPE: DNA
<213> ORGANISM: Artificial Sequence
```

-continued

```
<220> FEATURE:
<223> OTHER INFORMATION: Description of Artificial Sequence: Synthetic
      primer

<400> SEQUENCE: 18
gtgagcgcat gagagcccag cccggcaccc ctgtggccat tgaggaggaa ttctctctcc      60
tcacctgcag catcatctgt tacctcacct tcggagacaa gatcaaggac gacaacttaa     120
t                                                                     121

<210> SEQ ID NO 19
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ctgcaagcag tgacagtgcc cagggctctg atgtgtctct cacagcttgt aaagtgtgag      60
acagctgcct                                                            70

<210> SEQ ID NO 20
<211> LENGTH: 117
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgttcctctg aacaacaggg agaatatctc tgatcccacc tcaccattga gaaccagatt      60
tgtgtaccat ttgtctgacc tctgtaaaaa atgtgatcct acagaagtgg agctgga        117

<210> SEQ ID NO 21
<211> LENGTH: 93
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gaacaagatc ctcacagcca ccgtggacaa tgccaacatc ctgctacaga ttgacaatgc      60
ccgtctggct gctgatgact ccgcaccaa gtt                                   93

<210> SEQ ID NO 22
<211> LENGTH: 61
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tcccaatcga ccagtgtatc gacggctgag tgcacaggtg ccgccagctg ccgcaccagc      60
c                                                                     61

<210> SEQ ID NO 23
<211> LENGTH: 138
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 23
aaccaggaga aagtttcaga ctatgaaatg aagttgatgg atttagatgt tgaacaactt        60
ggaattccag aacaggagta cagctgtgta gtaaagatgc cttctggtga atttgcacgt       120
atatgccgag atctcagc                                                     138
```